(12) United States Patent
Park et al.

(10) Patent No.: US 11,104,728 B2
(45) Date of Patent: Aug. 31, 2021

(54) ANTI-EMAP II ANTIBODY AND USE THEREOF

(71) Applicant: HUB Biotech Co., Ltd., Seoul (KR)

(72) Inventors: Sang Gyu Park, Gyeonggi-do (KR); Gook-Jin Kang, Seoul (KR)

(73) Assignee: HUB Biotech Co., Ltd., Seoul (KR)

(*) Notice: Subject to any disclaimer, the term of this patent is extended or adjusted under 35 U.S.C. 154(b) by 0 days.

(21) Appl. No.: 16/497,612

(22) PCT Filed: Mar. 27, 2018

(86) PCT No.: PCT/KR2018/003569
§ 371 (c)(1),
(2) Date: Sep. 25, 2019

(87) PCT Pub. No.: WO2018/182266
PCT Pub. Date: Oct. 4, 2018

(65) Prior Publication Data
US 2020/0040071 A1    Feb. 6, 2020

(30) Foreign Application Priority Data

Mar. 27, 2017    (KR) .................. 10-2017-0038706

(51) Int. Cl.
| | |
|---|---|
| *A61K 39/00* | (2006.01) |
| *A61K 39/395* | (2006.01) |
| *C07K 16/00* | (2006.01) |
| *C07H 21/04* | (2006.01) |
| *C12P 21/06* | (2006.01) |
| *C12N 1/20* | (2006.01) |
| *C12N 15/74* | (2006.01) |
| *C07K 16/24* | (2006.01) |
| *A61P 19/02* | (2006.01) |
| *G01N 33/68* | (2006.01) |

(52) U.S. Cl.
CPC .............. *C07K 16/24* (2013.01); *A61P 19/02* (2018.01); *G01N 33/6854* (2013.01); *A61K 2039/505* (2013.01); *C07K 2317/24* (2013.01); *C07K 2317/52* (2013.01); *C07K 2317/565* (2013.01); *G01N 2800/2821* (2013.01)

(58) Field of Classification Search
None
See application file for complete search history.

(56) References Cited

U.S. PATENT DOCUMENTS

| | | | |
|---|---|---|---|
| 9,382,316 B2* | 7/2016 | Yoon ...................... | C07K 16/18 |
| 2002/0160957 A1 | 10/2002 | Stern et al. | |
| 2011/0028349 A1 | 2/2011 | Dave et al. | |
| 2011/0250701 A1* | 10/2011 | Kim ...................... | G01N 33/564 |
| | | | 436/501 |
| 2014/0154245 A1* | 6/2014 | Yoon ...................... | C07K 16/24 |
| | | | 424/133.1 |
| 2014/0221607 A1 | 8/2014 | Clauss et al. | |

FOREIGN PATENT DOCUMENTS

| | | |
|---|---|---|
| KR | 10-2010-0093451 | 8/2010 |
| KR | 10-2012-0118918 | 10/2012 |
| KR | 10-1420274 | 7/2014 |
| KR | 10-1757346 | 7/2017 |
| WO | WO88/07085 | 9/1988 |
| WO | WO88/07086 | 9/1988 |
| WO | WO88/09344 | 12/1988 |

OTHER PUBLICATIONS

Kwon et al. Identification of CD23 as a functional receptor for the proinflammatory cytokine AIMP1/p43. Journal of Cell Science 125, 4620-4629, 2012. (Year: 2012).*
Clarijs et al. EMAP-II expression is associated with macrophage accumulation in primary uveal melanoma. Invest Ophthalmol Vis Sci. May 2003;44(5):1801-6). (Year: 2003).*
Hou et al. Endothelial-monocyte-activating polypeptide II induces migration of endothelial progenitor cells via the chemokine receptor CXCR3. Experimental Hematology 34 (2006) 1125-1132. (Year: 2006).*
Behrensdorf et al., "The endothelial monocyte-activating polypeptide II (EMAP II) is a substrate for caspase-7", Federation of European Biochemical Societies Letters 466, 2000, pp. 143-147.
Bravo et al., "Analysis of crylAa expression in sigE and sigK mutants of Bacillus thuringiensis", Molecular and General Genetics, 1996, 250:734-741.
Herskowitz et al., "The Lysis-lysogeny Decision of the Phage λ: Explicit Programming and Responsiveness", Annual Review of Genetics, 1980, 14:399-445.
International Search Report in International Application No. PCT/KR2018/003569, dated Jun. 28, 2018, 2 pages.
Knies et al., "Regulation of Endothelial Monocyte-Activating Polypeptide II Release by Apoptosis", Proceedings of the National Academy of Sciences of the United States of America, Oct. 1998, 95:12322-12327.

(Continued)

*Primary Examiner* — Maher M Haddad

(74) *Attorney, Agent, or Firm* — Fish & Richardson P.C.

(57) ABSTRACT

The present invention relates to an anti-EMAP II antibody or an antigen-binding fragment thereof, a nucleic acid molecule for coding the same, or a preparation method thereof. Also, the present invention provides a method for using the anti-EMAP II antibody or the antigen-binding fragment thereof in preventing, treating or diagnosing EMAP II-mediated diseases, for example, TNF-α-mediated disease or Alzheimer's disease. Furthermore, the present invention provides a method for using the anti-EMAP II antibody or the antigen-binding fragment thereof in detecting or quantifying an EMAP II antigen. The antibody of the present invention may exhibit a more improved antigen-binding capacity compared to existing anti-EMAP antibodies and may treat the TNF-α-mediated disease more effectively.

14 Claims, 5 Drawing Sheets
Specification includes a Sequence Listing.

(56) References Cited

OTHER PUBLICATIONS

Lee et al., "Chapter 5 Cell Cultivations", Biochemical Engineering, Jan. 2001, 43 pages.
Park et al., "Optimization of Cry3A Yields in Bacillus thuringiensis by Use of Sporulation-Dependent Promoters in Combination with the STAB-SD mRNA Sequence", Applied and Environmental Microbiology, Oct. 1998, 64(10):3932-3938.
Trouet et al., "Targeting of Antitumor and Antiprotozoal Drugs by Covalent Linkage to Protein Carriers", Plenum Press: Institute of Cellular and Molecular Pathology, 1982, pp. 19-30.
Uhlmann et al., "Antisense Oligonucleotides: A New Therapeutic Principle", Chemical Reviews, Jun. 1990, 90(4):543-584.
Yanofksy et al., "Repression is Relieved Before Attenuation in the trp Operon of *Escherichia coli* as Tryptophan Starvation Becomes Increasingly Severe", Journal of Bacteriology, Jun. 1984, 158(3):1018-1024.
European Extended Search Report in EP Appln. No. 18776569.8, dated Dec. 16, 2020, 7 pages.

* cited by examiner (A)

(B)

SEQUENCE LISTING

<160> NUMBER OF SEQ ID NOS: 16

<210> SEQ ID NO 1
<211> LENGTH: 101
<212> TYPE: PRT
<213> ORGANISM: Artificial Sequence
<220> FEATURE:
<223> OTHER INFORMATION: BAP015-hum03-LC

<400> SEQUENCE: 1

Ala Ile Gln Leu Thr Gln Ser Pro Ser Ser Leu Ser Ala Ser Val Gly
1               5                   10                  15

Asp Arg Val Thr Ile Thr Cys Lys Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
50                  55                  60

Ser Gly Ser Gly Thr Asp Phe Thr Phe Thr Ile Ser Arg Leu Glu Pro
65                  70                  75                  80

Glu Asp Phe Ala Val Tyr Tyr Cys Gln Gln His Tyr Ser Ile Pro Tyr
                85                  90                  95

Thr Phe Gly Gln Gly
            100

<210> SEQ ID NO 2
<211> LENGTH: 106
<212> TYPE: PRT
<213> ORGANISM: Artificial Sequence
<220> FEATURE:
<223> OTHER INFORMATION: BAP015-hum03-HC

<400> SEQUENCE: 2

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Ser Tyr
            20                  25                  30

Thr Met His Trp Val Arg Gln Ala Pro Gly Gln Gly Leu Glu Trp Met
        35                  40                  45

Gly Tyr Ile Asn Pro Ser Ser Gly Phe Thr Asn Tyr Asn Gln Lys Phe
50                  55                  60

Lys Asp Arg Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Ser Arg Phe Ala Tyr Trp Gly Gln Gly
            100                 105

<210> SEQ ID NO 3
<211> LENGTH: 101
<212> TYPE: PRT
<213> ORGANISM: Artificial Sequence
<220> FEATURE:
<223> OTHER INFORMATION: BAP072-LC-T056W

<400> SEQUENCE: 3

Ala Ile Gln Leu Thr Gln Ser Pro Ser Ser Leu Ser Ala Ser Val Gly
1               5                   10                  15

Asp Arg Val Thr Ile Thr Cys Lys Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Trp Gly Val Pro Ser Arg Phe Ser Gly
50                  55                  60

Ser Gly Ser Gly Thr Asp Phe Thr Phe Thr Ile Ser Arg Leu Glu Pro
65                  70                  75                  80

Glu Asp Phe Ala Val Tyr Tyr Cys Gln Gln His Tyr Ser Ile Pro Tyr
                85                  90                  95

Thr Phe Gly Gln Gly
            100

<210> SEQ ID NO 4
<211> LENGTH: 106
<212> TYPE: PRT
<213> ORGANISM: Artificial Sequence
<220> FEATURE:
<223> OTHER INFORMATION: BAP072-CPS-15-HC

<400> SEQUENCE: 4

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Ser Tyr
                20                  25                  30

Thr Met His Trp Val Arg Gln Ala Pro Gly Gln Gly Leu Glu Trp Met
            35                  40                  45

Gly Tyr Ile Asn Pro Arg Ser Gly Phe Thr Asn Tyr Arg Gln Lys Phe
50                  55                  60

Lys His Arg Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Phe Ser Arg Phe Ala Tyr Trp Gly Gln Gly
            100                 105

<210> SEQ ID NO 5
<211> LENGTH: 101
<212> TYPE: PRT
<213> ORGANISM: Artificial Sequence
<220> FEATURE:
<223> OTHER INFORMATION: BAP072-LC-R54G

<400> SEQUENCE: 5

Ala Ile Gln Leu Thr Gln Ser Pro Ser Ser Leu Ser Ala Ser Val Gly
1               5                   10                  15

Asp Arg Val Thr Ile Thr Cys Lys Ala Ser Gln Asp Val Ser Thr Ala
                20                  25                  30

Val Ala Trp Tyr Gln Gln Lys Pro Gly Lys Ala Pro Lys Leu Leu Ile
            35                  40                  45

Tyr Ser Ala Ser Tyr Gly Tyr Thr Gly Val Pro Ser Arg Phe Ser Gly
50                  55                  60

Ser Gly Ser Gly Thr Asp Phe Thr Phe Thr Ile Ser Arg Leu Glu Pro
65                  70                  75                  80

Glu Asp Phe Ala Val Tyr Tyr Cys Gln Gln His Tyr Ser Ile Pro Tyr
                85                  90                  95

Thr Phe Gly Gln Gly
            100

<210> SEQ ID NO 6
<211> LENGTH: 106
<212> TYPE: PRT
<213> ORGANISM: Artificial Sequence
<220> FEATURE:
<223> OTHER INFORMATION: BAP072-CPS-08-HC

<400> SEQUENCE: 6

Glu Val Gln Leu Val Gln Ser Gly Ala Glu Val Lys Lys Pro Gly Ala
1               5                   10                  15
Thr Val Lys Ile Ser Cys Lys Val Ser Gly Tyr Thr Phe Thr Ser Tyr
            20                  25                  30
Thr Met His Trp Val Arg Gln Ala Pro Gly Gln Gly Leu Glu Trp Met
        35                  40                  45
Gly Tyr Thr Asn Pro Ser Ser Gly Phe Thr Asn Tyr Thr Gln Lys Phe
    50                  55                  60
Lys Asp Arg Val His Ile Ser Ala Asp Lys Ser Ile Ser Thr Ala Tyr
65                  70                  75                  80
Leu Gln Trp Ser Ser Leu Lys Ala Ser Asp Thr Ala Trp Tyr Tyr Cys
                85                  90                  95
Ala Ser Arg Phe Ala Tyr Trp Gly Gln Gly
            100                 105

<210> SEQ ID NO 7
<211> LENGTH: 11
<212> TYPE: PRT
<213> ORGANISM: Artificial Sequence
<220> FEATURE:
<223> OTHER INFORMATION: L-CDR1

<400> SEQUENCE: 7

Lys Ala Ser Gln Asp Val Ser Thr Ala Val Ala
1               5                   10

<210> SEQ ID NO 8
<211> LENGTH: 7
<212> TYPE: PRT
<213> ORGANISM: Artificial Sequence
<220> FEATURE:
<223> OTHER INFORMATION: L-CDR2a

<400> SEQUENCE: 8

Ser Ala Ser Tyr Arg Tyr Thr
1               5

<210> SEQ ID NO 9
<211> LENGTH: 7
<212> TYPE: PRT
<213> ORGANISM: Artificial Sequence
<220> FEATURE:
<223> OTHER INFORMATION: L-CDR2b

<400> SEQUENCE: 9

Ser Ala Ser Tyr Arg Tyr Trp
1               5

<210> SEQ ID NO 10
<211> LENGTH: 7
<212> TYPE: PRT
<213> ORGANISM: Artificial Sequence
<220> FEATURE:
<223> OTHER INFORMATION: L-CDR2c

<400> SEQUENCE: 10

Ser Ala Ser Tyr Gly Tyr Thr
1               5

<210> SEQ ID NO 11
<211> LENGTH: 9
<212> TYPE: PRT

```
<213> ORGANISM: Artificial Sequence
<220> FEATURE:
<223> OTHER INFORMATION: L-CDR3

<400> SEQUENCE: 11

Gln Gln His Tyr Ser Ile Pro Tyr Thr
1               5

<210> SEQ ID NO 12
<211> LENGTH: 10
<212> TYPE: PRT
<213> ORGANISM: Artificial Sequence
<220> FEATURE:
<223> OTHER INFORMATION: H-CDR1

<400> SEQUENCE: 12

Gly Tyr Thr Phe Thr Ser Tyr Thr Met His
1               5                   10

<210> SEQ ID NO 13
<211> LENGTH: 17
<212> TYPE: PRT
<213> ORGANISM: Artificial Sequence
<220> FEATURE:
<223> OTHER INFORMATION: H-CDR2a

<400> SEQUENCE: 13

Tyr Ile Asn Pro Ser Ser Gly Phe Thr Asn Tyr Asn Gln Lys Phe Lys
1               5                   10                  15

Asp

<210> SEQ ID NO 14
<211> LENGTH: 17
<212> TYPE: PRT
<213> ORGANISM: Artificial Sequence
<220> FEATURE:
<223> OTHER INFORMATION: H-CDR2b

<400> SEQUENCE: 14

Tyr Ile Asn Pro Arg Ser Gly Phe Thr Asn Tyr Arg Gln Lys Phe Lys
1               5                   10                  15

His

<210> SEQ ID NO 15
<211> LENGTH: 17
<212> TYPE: PRT
<213> ORGANISM: Artificial Sequence
<220> FEATURE:
<223> OTHER INFORMATION: H-CDR2c

<400> SEQUENCE: 15

Tyr Thr Asn Pro Ser Ser Gly Phe Thr Asn Tyr Thr Gln Lys Phe Lys
1               5                   10                  15

Asp

<210> SEQ ID NO 16
<211> LENGTH: 4
<212> TYPE: PRT
<213> ORGANISM: Artificial Sequence
```

```
<220> FEATURE:
<223> OTHER INFORMATION: H-CDR3

<400> SEQUENCE: 16

Arg Phe Ala Tyr
1
```

ANTI-EMAP II ANTIBODY AND USE THEREOF

TECHNICAL FIELD

The present invention relates to an anti-EMAP II antibody or an antigen-binding fragment thereof, a nucleic acid molecule for coding the same, or a preparation method thereof.

The present invention also relates to a method for using the anti-EMAP II antibody or the antigen-binding fragment thereof in preventing, treating or diagnosing EMAP II-mediated diseases, for example, TNF-α-mediated disease or Alzheimer's disease.

Furthermore, the present invention relates to a method for using the anti-EMAP II antibody or the antigen-binding fragment thereof in detecting or quantifying an EMAP II antigen.

BACKGROUND

An endothelial monocyte activating polypeptide II (EMAP II) is produced in such a way that a C-terminal region of p43 protein, i.e., a precursor protein, is isolated by means of an activated caspase-7 while apoptosis progresses (Behrensdorf et al., FEBS Lett. 466:143-147, 2000).

EMAP II, which is a factor for mediating pro-inflammatory responses, induces a tissue factor, a tumor necrosis factor (TNF) and interleukin-8 (IL-8) to be expressed in mononuclear phagocytes and polymorphonuclear leucocytes. Macrophages are accumulated in a tissue where EMAP II mRNA is overexpressed. This means that EMAP II is a chemotactic substance which induces the macrophages to dead cells. It is known that EMAP II acts as a cytokine and 15 amino acids of EMAP II N-terminus play an important role (Knies, U. E. et al., PNAS USA, 95:12322-12327, 1998, etc.).

The Korean Patent Publication No. 2010-0093451 discloses an anti-EMAP II monoclonal antibody specific to EMAP II (also referred to as "SCYE1") protein, and shows that such antibody may be used in diagnosing and treating inflammatory diseases; inhibits secretion of TNF-α mediating inflammatory responses; and exhibits an effect on treating Alzheimer's disease. Also, the Korean Patent Publication No. 2012-0118918 discloses an anti-EMAP II chimera or humanized antibody, of which immune responses are minimized in the human body, and shows that such antibody has the same binding capacity as a parent monoclonal antibody specifically binding to EMAP II.

If there is an antibody variant having an addition, deletion or substitution of an amino acid at a certain site in a heavy chain and/or light chain variable region of a parent antibody, and if such antibody variant shows a more improved antigen-antibody binding capacity than the parent antibody, it is found that such antibody variant may be administered more stably with less side effects, while exhibiting a therapeutic effect equal to or more than that of the parent antibody even in a smaller dosage thereof.

Against such technological backdrops, the present inventors have made every endeavor to develop an antibody specifically binding to EMAP II with a more improved antigen-binding capacity, and thus have developed a novel antibody with a more improved EMAP II binding capacity and a more excellent effect of inhibiting TNF-α and treating related diseases than existing antibodies, thereby completing the present invention.

DETAILED DESCRIPTION OF THE INVENTION

Technical Problem

One objective of the present invention is to provide an anti-EMAP II antibody or an antigen-binding fragment thereof with a more improved EMAP II antigen-binding capacity.

Other objective of the present invention is to provide a nucleic acid molecule for coding the antibody or the antigen-binding fragment thereof; a recombinant vector containing the nucleic acid molecule; a host cell having the recombinant vector transferred thereinto; and a method for producing the anti-EMAP II antibody or the antigen-binding fragment thereof by using the host cell.

Another objective of the present invention is to provide a composition for detecting an EMAP II antigen, containing the antibody or the antigen-binding fragment thereof; a kit for detection containing the same; and a method for detecting the EMAP II antigen by using the composition and the kit.

Yet another objective of the present invention is to provide a composition for preventing or treating EMAP II-mediated diseases, for example, TNF-α-mediated disease or Alzheimer's disease, containing the antibody or the antigen-binding fragment thereof.

Technical Solution

This is described in detail as follows. Meanwhile, each description and embodiment disclosed in the present invention may be applied to other descriptions and embodiments thereof, respectively. In other words, all the combinations of various elements disclosed in the present invention fall within the scope of the present invention. Also, it may not be seen that the scope of the present invention is limited to the specific descriptions described below.

1. Anti-EMAP II Antibody and Antigen-Binding Fragment Thereof

In one aspect of the present invention for achieving the objectives, there is provided an anti-EMAP II antibody or an antigen-binding fragment thereof with an improved antigen-binding capacity.

The anti-EMAP II antibody or the antigen-binding fragment thereof according to the present invention binds to EMAP II with a higher affinity compared to existing antibodies and inhibits an activity thereof, thereby exhibiting an excellent TNF-α inhibition effect. Thus, such antibody may be valuably used in preventing or treating EMAP II-mediated diseases, for example, TNF-α-mediated disease or Alzheimer's disease for itself or along with conventional, pharmaceutically acceptable carriers, etc.

The anti-EMAP II antibody of the present invention contains a light chain variable region, including a light chain CDR1 consisting of SEQ ID NO: 7, a light chain CDR2 consisting of SEQ ID NO: 9, and a light chain CDR3 consisting of SEQ ID NO: 11; and a heavy chain variable region, including a heavy chain CDR1 consisting of SEQ ID NO: 12, a heavy chain CDR2 consisting of SEQ ID NO: 14, and a heavy chain CDR3 consisting of SEQ ID NO: 16.

In one specific embodiment of the anti-EMAP II antibody according to the present invention, the anti-EMAP II antibody may contain a light chain variable region consisting of SEQ ID NO: 3; and a heavy chain variable region consisting of SEQ ID NO: 4.

Preferably, the antibody may be a humanized antibody, and particularly may contain a human kappa or IgG-derived constant region, but is not limited thereto.

As used herein, the term "antibody" means a protein molecule serving as a receptor, which specifically recognizes an antigen, including an immunoglobulin molecule immunologically having reactivity with a certain antigen. As an example, such antibody may include a monoclonal antibody, a polyclonal antibody, a full-length antibody and an antibody fragment all. Also, the term "antibody" may include a bivalent or dual-specificity molecule (e.g., a dual-specificity antibody), a diabody, a triabody or a tetrabody.

As used herein, the term "monoclonal antibody" refers to an antibody molecule of a single molecular composition obtained from a group of substantially identical antibodies, wherein this monoclonal antibody shows a single binding property and affinity to a certain epitope, while the polyclonal antibody may bind to several epitopes. As used herein, the term "full-length antibody" takes on a structure of having two full-length light chains and two full-length heavy chains, wherein each light chain is linked to a heavy chain by disulfide bonding. A heavy chain constant region has a gamma (γ), mu (μ), alpha (α), delta (δ) and epsilon (ε) type, and also has a gamma 1 (γ1), gamma 2 (γ2), gamma 3 (γ3), gamma 4 (γ4), alpha 1 (α1) and alpha 2 (α2) as a subclass. A light chain constant region has a kappa (κ) and lambda (λ) type. IgG includes IgG1, IgG2, IgG3 and IgG4 as a subtype.

As used herein, the term "heavy chain" may include both a full-length heavy chain and a fragment thereof, containing a variable region VH including an amino acid sequence with a variable region sequence enough to give specificity to an antigen; as well as three constant regions CH1, CH2 and CH3. Also, as used herein, the term "light chain" may include both a full-length light chain and a fragment thereof, containing a variable region VL including an amino acid sequence with a variable region sequence enough to give specificity to an antigen; as well as a constant region CL.

As used herein, the term "antibody variant" means a variant, in which a part of an amino acid sequence of a parent antibody is substituted, added or deleted to improve an antibody affinity, etc., more than the parent antibody, and includes a chimera antibody, a humanized antibody, etc. The antibody of the present invention, which is a variant of an antibody disclosed in the Korean Patent Publication No. 2012-0118918, is used herein along with an "anti-EMAP II antibody" and an "anti-EMAP II antibody variant."

As used herein, the term "chimera antibody," which is created by recombining a variable region of a mouse antibody and a constant region of a human antibody, is an antibody which has a great improvement in immune responses compared to the mouse antibody.

As used herein, the term "humanized antibody" means an antibody, which is modified in such a way that a protein sequence of an antibody derived from non-human species becomes similar to an antibody naturally produced from humans. As an example, the humanized antibody may be prepared by recombining a mouse-derived CDR with a human antibody-derived FR to prepare a humanized variable region, and then by recombining the same with a constant region of a preferable human antibody. However, if only CDR grafting is simply performed, the affinity of the humanized antibody becomes low. Thus, such low affinity may be raised up to the same level as the affinity of an original mouse antibody, in such a way that several important FR amino acid residues considered to have an influence on a three-dimensional structure of the CDR are allowed to have more affinity with those of the mouse antibody.

The present invention also provides an antigen-binding fragment of the anti-EMAP II antibody. The antigen binding fragment may be Fab, F(ab'), F(ab')2 or Fv.

As used herein, the terms "fragment," "antibody fragment" and "antigen-binding fragment" refer to any fragments of the inventive antibody, which hold an antigen-binding function of the antibody, wherein such terms are interchangeably used with each other. An exemplary antigen-binding fragment includes Fab, Fab', $F(ab')_2$, Fv and the like, but is not limited thereto.

The Fab has one antigen-binding site, which takes on a structure of having light chain and heavy chain variable regions; a light chain constant region; and a first constant region (CH1 domain) of a heavy chain. With regard to an antibody molecule, its antigen-binding fragment or an antibody fragment means a fragment which holds an antigen-binding function, wherein Fab' has a difference from Fab, in that Fab' has a hinge region containing at least one cysteine residue at C terminus of a heavy chain CH1 domain. F(ab')2 antibody is produced in such a way that a cysteine residue of the hinge region of Fab' forms disulfide bonding. Fv is a minimum antibody fragment having only a heavy chain variable region and a light chain variable region, wherein a recombination technology for producing an Fv fragment is disclosed in the International Patent Publication filed under the patent cooperation treaty (PCT) WO 88/07085, WO 88/07086, WO 88/09344 and the like. In case of two-chain Fv, a heavy chain variable region and a light chain variable region are linked to each other by means of non-covalent bonding. In case of single-chain Fv, a heavy chain variable region and a single chain variable region are linked to each other by means of covalent bonding generally via a peptide linker, or directly linked to each other at C-terminus, and thus may form a structure like a dimer, as shown in the two-chain Fv. Such antibody fragment may be obtained by using protease (for example, Fab may be obtained by performing restriction digestion of a whole antibody with papain, while F(ab')2 fragment may be obtained by doing so with pepsin), and may be preferably prepared by means of a gene recombination technology.

Also, the antibody or the antigen-binding fragment thereof according to the present invention may contain a sequence of the anti-EMAP II antibody described herein as well as biological equivalents thereof, within the range that may show an improvement in the EMAP II antigen-binding capacity. For example, an amino acid sequence of the antibody may be further given a change, in order to more improve the binding affinity and/or other biological characteristics of the antibody. Such modification includes, for example, the deletion, insertion and/or substitution of an amino acid sequence residue of the antibody. Such amino acid mutation is performed on the basis of the relative similarity of amino acid side chain substituents, e.g., hydrophobicity, hydrophilicity, charges, sizes, etc. According to an analysis of sizes, shapes and types of the amino acid side chain substituents, it might be seen that arginine, lysine and histidine are all positively charged residues; alanine, glycine and serine have similar sizes; and phenylalanine, tryptophan and tyrosine have similar shapes. Thus, in this regard, it might be seen that arginine, lysine and histidine; alanine, glycine and serine; and phenylalanine, tryptophan and tyrosine are biologically functional equivalents.

In one specific embodiment of the present invention, the anti-EMAP II antibody of the present invention has an amino acid sequence with only four amino acids substituted therein compared to another antibody, i.e., a comparison target, but shows such a remarkable effect that an antigen-antibody binding capacity of the former one is improved 10 times more than the latter one (FIGS. 2 and 3).

Also, in another specific embodiment of the present invention, it was identified in case of administering the inventive anti-EMAP II antibody into an arthritis-induced mouse that such case achieves an excellent effect of inhibiting TNF-α secretion as well as an excellent effect of treating arthritis symptoms (FIGS. 4 and 5).

2. Nucleic Acid Molecule for Coding Anti-Emap II Antibody or Antigen-Binding Fragment Thereof; Recombinant Vector; Transformant; and Method for Preparing the Same
2-1. Nucleic Acid Molecule for Coding EMAP II Antibody or Antigen-Binding Fragment Thereof In another aspect of the present invention, there is provided a nucleic acid molecule for coding the antibody or the antigen-binding fragment thereof. The antibody and the antigen-binding fragment thereof are the same as described above.

As used herein, the term "nucleic acid molecule" has a meaning comprehensively including DNA (gDNA and cDNA) and RNA molecules, wherein a nucleotide, i.e., a basic unit of the nucleic acid molecule, includes a natural nucleotide as well as an analogue with a sugar or base site modified therein (Scheit, Nucleotide Analogs, John Wiley, New York (1980); Uhlman and Peyman, Chemical Reviews (1990) 90:543-584). A sequence of the nucleic acid molecule for coding light chain and heavy chain variable regions according to the present invention may be modified, wherein the modification includes the addition, deletion, or non-conservative or conservative substitution of the nucleotide.

According to one exemplary embodiment of the present invention, the nucleic acid molecule for coding an antibody or an antigen-binding fragment thereof according to the present invention may include a nucleic acid molecule for coding a light chain CDR1 consisting of amino acid sequence of SEQ ID NO: 7, a nucleic acid molecule for coding a light chain CDR2 consisting of amino acid sequence of SEQ ID NO: 9, and a nucleic acid molecule for coding a light chain CDR3 consisting of amino acid sequence of SEQ ID NO: 11; and a nucleic acid molecule for coding a heavy chain CDR1 consisting of amino acid sequence of SEQ ID NO: 12, a nucleic acid molecule for coding a heavy chain CDR2 consisting of amino acid sequence of SEQ ID NO: 14, and a nucleic acid molecule for coding a heavy chain CDR3 consisting of amino acid sequence of SEQ ID NO: 16.

In a preferred aspect of the exemplary embodiment above, the nucleic acid molecule may include a nucleic acid molecule for coding a light chain variable region consisting of amino acid sequence of SEQ ID NO: 3, and a nucleic acid molecule for coding a heavy chain variable region consisting of amino acid sequence of SEQ ID NO: 4, but is not limited thereto.

2-2. Recombinant Vector Containing Nucleic Acid Molecule

In another aspect of the present invention, there is provided a recombinant vector containing the nucleic acid molecule.

As used herein, the term "vector," which serves as a means for expressing a target gene in a host cell, includes a plasmid vector; a cosmid vector; a virus vector such as a bacteriophage vector, an adenovirus vector, a retrovirus vector and an adeno-associated virus vector; and the like, and may be preferably the plasmid vector, but is not limited thereto.

According to one exemplary embodiment of the present invention, the recombinant vector containing the nucleic acid molecule according to the present invention may contain a base sequence of a light chain variable region, including a nucleic acid molecule for coding a light chain CDR1 consisting of amino acid sequence of SEQ ID NO: 7, a nucleic acid molecule for coding a light chain CDR2 consisting of amino acid sequence of SEQ ID NO: 9, and a nucleic acid molecule for coding a light chain CDR3 consisting of amino acid sequence of SEQ ID NO: 11; and/or a base sequence of a heavy chain variable region, including a nucleic acid molecule for coding a heavy chain CDR1 consisting of amino acid sequence of SEQ ID NO: 12, a nucleic acid molecule for coding a heavy chain CDR2 consisting of amino acid sequence of SEQ ID NO: 14, and a nucleic acid molecule for coding a heavy chain CDR3 consisting of amino acid sequence of SEQ ID NO: 16.

In a preferred aspect of the exemplary embodiment above, the vector may contain a nucleic acid molecule for coding a light chain variable region consisting of amino acid sequence of SEQ ID NO: 3, and/or a nucleic acid molecule for coding a heavy chain variable region consisting of amino acid sequence of SEQ ID NO: 4, but is not limited thereto.

In the vector of the present invention, the nucleic acid molecule for coding a light chain variable region and the nucleic acid molecule for coding a heavy chain variable region may be operatively linked to a promoter.

As used herein, the term "operatively linked" means a functional linkage between a nucleic acid expression control sequence (e.g., a promoter, a signal sequence or an array of transcriptional regulatory factor binding sites) and another nucleic acid sequence, wherein the control sequence regulates the transcription and/or translation of the another nucleic acid sequence.

A recombinant vector system of the present invention may be constructed by means of various methods known in the art, wherein a detailed method thereof is disclosed in Sambrook et al., Molecular Cloning, A Laboratory Manual, Cold Spring Harbor Laboratory Press (2001) and this document is incorporated herein by reference.

The vector of the present invention may be typically constructed as a vector for cloning or a vector for expression. The recombinant vector of the present invention is preferably an expression vector. Also, the vector of the present invention may be constructed in such a way that a prokaryotic cell or a eukaryotic cell is a host.

For example, if the vector of the present invention is the expression vector and the prokaryotic cell is the host, it is common to include a strong promoter capable of performing transcription (e.g., a tac promoter, a lac promoter, a lacUV5 promoter, a lpp promoter, a pLλ promoter, a pRλ promoter, a rac5 promoter, an amp promoter, a recA promoter, an SP6 promoter, a trp promoter, a T7 promoter and the like); a ribosome binding site for initiation of decoding; and a transcription/decoding termination sequence. If *E. coli* (e.g., HB101, BL21, DH5α, etc.) is used as the host cell, a promoter and operator region of *E. coli* tryptophan biosynthetic pathway (Yanofsky, C., J. Bacteriol., (1984) 158: 1018-1024) and a left-oriented promoter of phage λ (pLλ promoter, Herskowitz, I. and Hagen, D., Ann. Rev. Genet., (1980) 14:399-445) may be used as a regulatory region. If *Bacillus* is used as the host cell, a promoter of a toxoprotein gene of *Bacillus thuringiensis* (Appl. Environ. Microbiol. (1998) 64:3932-3938; Mol. Gen. Genet. (1996) 250:734-741) or any promoters expressible in *Bacillus* may be used as the regulatory region.

Meanwhile, the recombinant vector of the present invention may be prepared by manipulating plasmids (e.g., pCL, pSC101, pGV1106, pACYC177, ColE1, pKT230, pME290, pBR322, pUC8/9, pUC6, pBD9, pHC79, pIJ61, pLAFR1, pHV14, pGEX series, pET series, pUC19 and the like), phages (e.g., Δgt4·ΔB, λ-Charon, λΔz1, M13 and the like) or virus (e.g., SV40, etc.), which are often used in the art. For example, the recombinant vector of the present invention may be prepared by manipulating a pCL expression vector, particularly a pCLS05 (Korean Patent Registration No. 10-1420274) expression vector, but is not limited thereto.

Meanwhile, if the vector of the present invention is the expression vector and the eukaryotic cell is the host, the followings may be used: the promoters derived from genome of mammal cells (e.g., a metallothionein promoter, a β-actin promoter, a human hemoglobin promoter and a human muscle creatine promoter) or the promoters derived from mammal virus (e.g., an adenovirus late promoter, a vaccinia virus 7.5K promoter, an SV40 promoter, a cytomegalo virus (CMV) promoter, a tk promoter of HSV, a mouse breast tumor virus (MMTV) promoter, an LTR promoter of HIV, a promoter of moloney virus, a promoter of epstein-barr virus (EBV) and a promoter of rous sarcoma virus (RSV)), while generally having a polyadenylation sequence as a transcription termination sequence. Particularly, the recombinant vector of the present invention may contain the CMV promoter.

The recombinant vector of the present invention may be fused with other sequences such that an antibody expressed therefrom may be easily purified. As a fused sequence, there are, for example, a glutathione S-transferase (Pharmacia, USA), a maltose binding protein (NEB, USA), FLAG (IBI, USA), 6× His (hexahistidine; Quiagen, USA) and the like. Also, because the protein expressed by means of the vector of the present invention is an antibody, such expressed antibody may be easily purified via a protein A column, etc., without an additional sequence for purification.

Meanwhile, the recombinant vector of the present invention contains an antibiotic resistance gene conventionally used as a selectable marker in the art, and may contain, for example, genes resistant to ampicillin, gentamicin, carbenicillin, chloramphenicol, streptomycin, kanamycin, geneticin, neomycin and tetracycline.

The vector for expressing an antibody according to the present invention may be a vector system, in which a light chain and a heavy chain are simultaneously expressed in one vector, or a system for expressing a light chain and a heavy chain in a separate vector, respectively, wherein both systems are available. In case of the latter one, both vectors are transferred into a host cell through co-transformation and targeted transformation. Co-transformation is a method, in which each of vector DNAs for coding a light chain and a heavy chain is concurrently transferred into the host cell, after which a cell of expressing both the light chain and the heavy chain is selected. Targeted transformation is a method, in which a cell transformed with the vector containing the light chain (or the heavy chain) is selected, after which a resulting selected cell of expressing the light chain is transformed again with the vector containing the heavy chain (or the light chain), such that a cell of expressing both the light chain and the heavy chain is finally selected.

2-3. Transformant Containing Recombinant Vector

In another aspect of the present invention, there is provided a host cell containing the recombinant vector. Preferably, the host cell of the present invention is the host cell transformed with the recombinant vector.

The host cell capable of stably and continuously cloning and expressing the vector of the present invention may be any host cells known in the art, wherein such host cell includes, for example, *Bacillus* species strains such as *Escherichia coli*, *Bacillus subtilis* and *Bacillus thuringiensis*; and prokaryotic host cells such as *Streptomyces*, *Pseudomonas* (for example, *Pseudomonas putida*), *Proteus mirabilis* or *Staphylococcus* (for example, *Staphylococcus carnosus*), but is not limited thereto.

A suitable eukaryotic host cell transformed with the vector may be fungi such as *Aspergillus* species; yeasts such as *Pichia pastoris, Saccharomyces cerevisiae, Schizosaccharomyces* and *Neurospora crassa*; other lower eukaryotic cells; higher eukaryotic cells such as insect-derived cells; and plant or mammal-derived cells, but is not limited thereto.

Particularly, the host cell may be monkey kidney cells 7 (COS7), NSO cells, SP2/0, Chinese hamster ovary (CHO) cells, W138, baby hamster kidney (BHK) cells, MDCK, myeloma cell lines, HuT 78 cells or 293 cells, and more particularly may be the CHO cells, but is not limited thereto.

In case of using microorganisms such as *E. coli*, etc., productivity tends to be higher compared to that of using animal cells, etc. However, such use is not preferable to produce intact Ig type antibodies due to a glycosylation problem, but may be used in production of Fab, Fv and the like.

In the present invention, "transformation" and/or "transfection" into host cells includes any methods for transferring a nucleic acid into organisms, cells, tissues or organs, and may be performed by selecting a suitable standard technology according to host cells as known in the art. The methods as above include electroporation, protoplast fusion, calcium phosphate ($CaPO_4$) precipitation, calcium chloride ($CaCl_2$) precipitation, agitation with silicon carbide fibers, agrobacteria-mediated transformation, PEG, dextran sulfate, lipofectamine, drying/inhibition-mediated transformation methods and the like, but are not limited thereto.

2-4. Method for Preparing EMAP II Antibody or Antigen-Binding Fragment Thereof

In another aspect of the present invention, there is provided a method for preparing an anti-EMAP II antibody or an antigen-binding fragment thereof, including a step of culturing a transformed cell of the present invention. Preferably, the method for preparing an anti-EMAP II antibody or an antigen-binding fragment thereof according to the present invention may further include a step of expressing an anti-EMAP II antibody or an antigen-binding fragment thereof in cultured transformed cells.

In the method for preparing an antibody or an antigen-binding fragment thereof, a culture of transformed cells may be performed according to appropriate media and culture conditions known in the art. Such culture process may be easily adjusted and used by those skilled in the art according to selected strains. Such various culture methods are disclosed in various documents (for example, James M. Lee, Biochemical Engineering, Prentice-Hall International Editions, 138-176). Cell culture is classified into suspension culture and attachment culture according to cell growth modes; and into the batch, fed-batch and continuous types of culture methods according to culture methods. A medium used in culture should appropriately satisfy the requirements for certain strains.

In animal cell culture, the medium contains a variety of carbon sources, nitrogen sources and microelement components. An example of carbon sources available may include carbohydrates such as glucose, sucrose, lactose, fructose, maltose, starch and cellulose; fats such as soybean oil, sunflower oil, castor oil and coconut oil; fatty acids such as palmitic acid, stearic acid and linoleic acid; alcohols such as glycerol and ethanol; and organic acids such as acetic acid, wherein such carbon sources may be used alone or in combination.

A nitrogen source available in the present invention may include, for example, organic nitrogen sources such as peptone, yeast extract, gravy, malt extract, corn steep liquor (CSL), soybean and wheat; and inorganic nitrogen sources such as urea, ammonium sulfate, ammonium chloride, ammonium phosphate, ammonium carbonate and ammonium nitrate, wherein such nitrogen sources may be used alone or in combination. The medium may include potassium dihydrogen phosphate, dipotassium hydrogen phosphate and sodium-containing salts corresponding thereto as a phosphorus source. Also, the medium may include metallic salts such as magnesium sulfate or iron sulfate. Besides, amino acids, vitamins, appropriate precursors and the like may be included therein.

During culture, compounds such as ammonium hydroxide, potassium hydroxide, ammonia, phosphoric acid and sulfuric acid may be added into a culture product in an appropriate manner, such that pH of such culture product may be adjusted. During culture, antifoaming agents such as fatty acid polyglycol ester may be also used to inhibit foams from being created. Furthermore, oxygen or oxygen-containing gases (e.g., air) are injected into the culture product such that the culture product may maintain an aerobic state thereof. A temperature of the culture product may be generally 20 to 45° C., preferably 25 to 40° C., but is not limited thereto.

An antibody obtained from culturing a transformed host cell may be used in a non-purified state, and may be also used in such a way that the antibody is purified with high purity by further using various conventional methods, for example, dialysis, salt precipitation, chromatography and the like. Out of them, a method using chromatography has been most often used, wherein a type and order of columns may be selected from ion exchange chromatography, size exclusion chromatography, affinity chromatography, etc. according to antibody characteristics, culture methods, etc.

3. Use of Anti-EMAP II Antibody or Antigen-Binding Fragment Thereof for Detecting EMAP II Antigen In another aspect of the present invention, there are provided a composition for detecting an EMAP II antigen, containing the antibody or the antigen-binding fragment thereof; a kit for detection containing the same; and a method for detecting an EMAP II antigen using the composition and the kit.

The composition for detecting EMAP II and the kit containing the same may effectively detect EMAP II, in such a way that the anti-EMAP II antibody or the antigen-binding fragment thereof according to the present invention is brought into contact with a sample to form an antigen-antibody complex.

As used herein, the term "antigen-antibody complex" means a combination between EMAP II and an antibody recognizing the same, so as to identify a presence or abundance of EMAP II in the sample.

A method for quantifying an EMAP II antigen using the composition for detecting EMAP II and the kit containing the same may be performed by identifying a formation of an antigen-antibody complex, wherein the formation of the antigen-antibody complex may be identified by means of enzyme-linked immunosorbent assay (ELISA), western blotting, immunofluorescence, immunohistochemistry staining, flow cytometry, immunocytochemistry, radioimmunoassay (RIA), immunoprecipitation assay, immunodiffusion assay, complement fixation assay, protein chip or the like, but is not limited thereto. ELISA includes various ELISA methods such as a direct ELISA, which uses a labeled antibody of recognizing an antigen attached to a solid support; an indirect ELISA, which uses a labeled secondary antibody of recognizing a capture antibody in an antibody complex of recognizing an antigen attached to a solid support; a direct sandwich ELISA, which uses another labeled antibody of recognizing an antigen in an antibody-antigen complex attached to a solid support; an indirect sandwich ELISA, which carries out reaction with another antibody of recognizing an antigen in an antibody-antigen complex attached to a solid support, and then uses a labeled secondary antibody of recognizing this antibody; etc.

As a label for allowing the formation of antigen-antibody complex to be qualitatively or quantitatively measurable, there are enzymes, fluorescent materials, ligands, luminous materials, microparticles, redox molecules, radio isotopes and the like, but not necessarily limited thereto. As the enzymes, there are β-glucuronidase, β-D-glucosidase, β-D-galactosidase, urease, peroxidase, alkaline phosphatase, acetylcholinesterase, glucose oxidase, hexokinase and GDPase, RNase, glucose oxidase and luciferase, phosphofructokinase, phosphoenolpyruvate carboxylase, aspartate aminotransferase, phosphoenolpyruvate decarboxylase, β-lactamase, etc., but not limited thereto.

4. Pharmaceutical Use of Anti-EMAP II Antibody or Antigen-Binding Fragment Thereof An antibody or an antigen-binding fragment thereof according to the present invention may bind to EMAP II with a high affinity and thus such antibody may be used in diagnosing, treating or preventing EMAP II-mediated diseases, for example, TNF-α-mediated disease or Alzheimer's disease for itself or along with conventional, pharmaceutically acceptable carriers. The antibody or the antigen-binding fragment thereof is the same as described above.

The antibody or the antigen-binding fragment thereof according to the present invention may be used in a form of pharmaceutical compositions, quasi drug compositions and health food compositions.

In an aspect of the present invention, there is provided a pharmaceutical composition for preventing or treating EMAP II-mediated diseases, containing the inventive antibody or the antigen-binding fragment thereof as an active ingredient.

The antibody or the antigen-binding fragment thereof according to the present invention effectively inhibits TNF-α secretion by binding to EMAP II and inhibiting an activity thereof, and thus may be used in preventing or treating TNF-α-mediated diseases.

Particularly, in an aspect of the present invention, there is provided a pharmaceutical composition for preventing or treating TNF-α-mediated diseases, containing the inventive antibody or the antigen-binding fragment thereof as an active ingredient. The TNF-α-mediated diseases include adult respiratory distress syndrome, lack of appetite, cancer, chronic fatigue syndrome, graft-versus-host rejection, hyperalgesia, inflammatory bowel disease, neuroinflammatory disease, ischemia including cerebral ischemia or reperfusion injury, trauma, epilepsy, brain damage resulting from bleeding or seizure, diabetes, multiple sclerosis, eye disease, pain, pancreatitis, pulmonary fibrosis, rheumatoid arthritis, osteoarthritis, seronegative polyarthritis, ankylosing spondylitis, Reiter's syndrome, reactive arthritis, psoriatic arthritis, enteropathic arthritis, polymyositis, dermatomyositis, scleroderma, systemic sclerosis, vasculitis, cerebral vasculitis, Sjogren's syndrome, rheumatic fever, polychondritis and polymyalgia, rheumatoid and giant cell arteritis, septic shock, side effects resulting from radiotherapy, systemic lupus erythematosus, temporomandibular disease and thyroiditis, but are not limited thereto.

In another aspect of the present invention, there is provided a pharmaceutical composition for preventing or treating Alzheimer's disease, containing the inventive antibody or the antigen-binding fragment thereof as an active ingredient.

As used herein, the term "prevention" means all the acts, which inhibit a disease or delay a progress thereof by administering the composition of the present invention, while "treatment" means the inhibition, reduction or elimination of a development of a disease.

A pharmaceutical composition of the present invention may further contain pharmaceutically acceptable carriers, wherein the pharmaceutically acceptable carriers are ones conventionally used in formulating a preparation, including, but not limited thereto, lactose, dextrose, sucrose, sorbitol, mannitol, starch, acacia rubber, calcium phosphate, alginate, gelatin, calcium silicate, microcrystalline cellulose, polyvinyl pyrrolidone, cellulose, water, syrup, methyl cellulose, methyl hydroxybenzoate, propylhydroxybenzoate, talc, magnesium stearate, mineral oil and the like. A composition for preventing or treating cancer according to the present invention may further contain lubricants, humectants, sweetening agents, flavoring agents, emulsifiers, suspending agents, preservatives, etc. in addition to the components above. Suitable, pharmaceutically acceptable carriers and preparations are described in detail in a document [Remington's Pharmaceutical Sciences (19th ed., 1995)].

The pharmaceutical composition of the present invention may be orally or parenterally administered, wherein the parenteral administration may be performed by means of intravenous infusion, subcutaneous infusion, intramuscular infusion, intraperitoneal infusion, endodermis administration, local administration, intranasal administration, intrapulmonary administration, intrarectal administration and the like. Upon oral administration, protein or peptide is digested. Thus, an oral composition may be formulated into dosage forms in such a way that an active drug thereof is coated or protected from being decomposed in the stomach, wherein the composition of the present invention may be administered by means of any devices capable of moving an active substance into a target cell.

A suitable dosage of the pharmaceutical composition according to the present invention may vary depending on factors such as a method for formulating a preparation, an administration mode, a patient's age, weight, gender, pathological condition, food, administration time, administration route, excretion rate and reaction sensitivity, wherein ordinarily skilled doctors may easily determine and prescribe an effective dosage for a desired treatment or prevention. According to one exemplary embodiment of the present invention, a daily dosage of the inventive pharmaceutical composition may be 0.1-100 mg/kg, preferably 0.1-10 mg/kg and more preferably 0.1-2 mg/kg. As used herein, the term "pharmaceutically effective amount" means an amount enough to treat, prevent and diagnose diseases.

The pharmaceutical composition of the present invention may be formulated into preparations by using pharmaceutically acceptable carriers and/or excipients according to a method easily practicable by those skilled in the art to which the present invention pertains, and thus may be prepared in a unit dose form or prepared by being inserted into a multi-dose container. At that time, a dosage form may be in a form of solutions, suspensions or emulsions in oily or aqueous media, or may be in a form of extracts, powders, suppositories, granules, tablets or capsules, and may further contain dispersing agents or stabilizing agents.

The composition of the present invention may be administered as an individual therapeutic agent or in combination with other therapeutic agents, and may be administered sequentially or simultaneously with a conventional therapeutic agent.

An antibody or an antigen-binding fragment thereof according to the present invention may be administered in vivo in a form of antibody-drugs (functional molecules) and dual specificity antibody-drug (functional molecules) conjugates and thus may be used in treating cancer, wherein descriptions thereof are the same as described above. Several appropriate and preferred conditions for targeting drugs into specific target regions are reported, for example, in a document [Trouet et al., Plenum Press, New York and London, (1982) 19-30].

The antibody or the antigen-binding fragment thereof according to the present invention may be further combined with functional molecules or administered in combination therewith, and thus may be used in preventing, treating and diagnosing EMAP II-related diseases. The functional molecules may include chemicals, radioactive nuclides, immunotherapy agents, cytokine, chemokine, toxin, biological agents, enzyme inhibitors and the like.

In one specific embodiment of the present invention, it was identified in case of administering the pharmaceutical composition of the present invention into a collagen-induced arthritis (CIA) mouse model that there is distinctively an alleviation in arthritis scores and a decrease in foot thickness (FIG. 4), and that there is an excellent effect of inhibiting TNF-α levels in blood (FIG. 5). Thus, the pharmaceutical composition of the present invention may be used as a therapeutic agent for EAMP II-mediated diseases, including TNF-α-mediated disease.

In another aspect of the present invention, there is provided a method for diagnosing, preventing or treating EMAP II-mediated diseases, for example, TNF-α-mediated disease or Alzheimer's disease, including a step of administering a pharmaceutically effective amount of the inventive antibody or the antigen-binding fragment thereof into subjects, e.g., humans or mammals excluding the humans. Also, the present invention provides a method for diagnosing EMAP II-mediated diseases, for example, TNF-α-mediated disease or Alzheimer's disease, including a step of administering the inventive antibody or the antigen-binding fragment thereof into subjects in need, e.g., humans or mammals excluding the humans.

As used herein, the term "individual" means all the animals including monkeys, cows, horses, sheep, pigs, chickens, turkeys, quails, cats, dogs, mice, rats, rabbits or guinea pigs, as well as humans, who have developed the EMAP II-mediated diseases or are likely to do so.

In another aspect of the present invention, there is provided a use of the inventive antibody or the antigen-binding fragment thereof in preparing a drug for preventing or treating EMAP II-mediated diseases, for example, TNF-α-mediated disease or Alzheimer's disease.

Advantageous Effects

An anti-EMAP II antibody of the present invention binds to an EMAP II antigen with a higher affinity and exhibits a more excellent effect of preventing and treating EMAP II-mediated diseases, for example, TNF-α-mediated disease or Alzheimer's disease compared to existing antibodies.

Thus, the antibody or the antigen-binding fragment thereof according to the present invention may be valuably used in detecting an EMAP II antigen, or preventing, treating or diagnosing EMAP II-mediated diseases.

MODE FOR INVENTION

Figure 1:
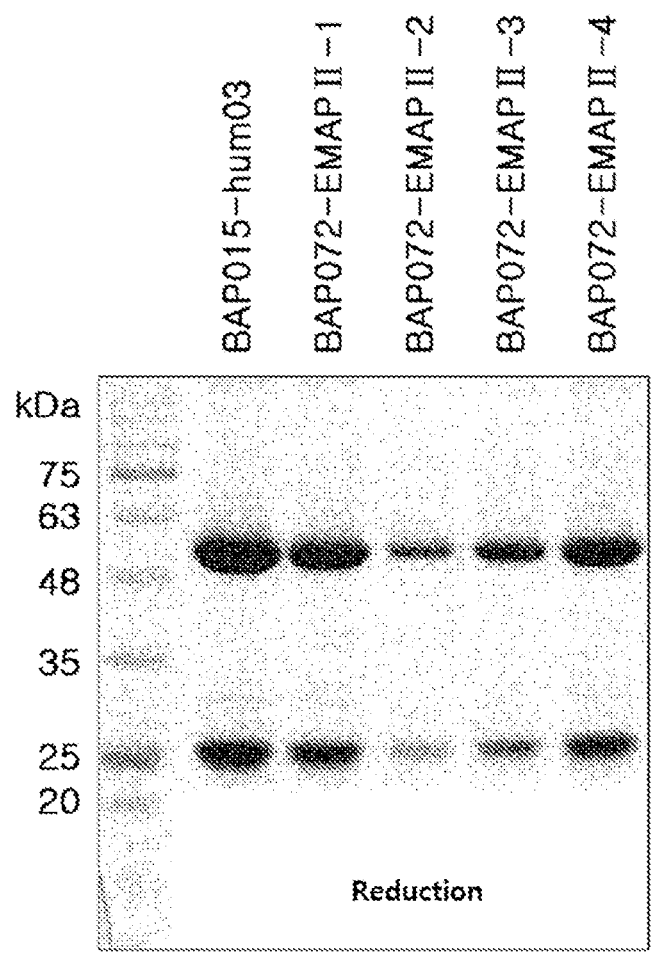
FIG. 1 shows results of identifying an anti-EMAP II antibody of the present invention under reducing conditions by using SDS-PAGE.

Hereinafter, the present invention will be described in more detail through exemplary embodiments. These exemplary embodiments are provided only for the purpose of illustrating the present invention in more detail, and thus it will be apparent to those skilled in the art that the scope of the present invention is not limited thereto according to the gist of the present invention.

Example 1. Preparation for Anti-EMAP II Antibody

Example 1-1. Securing Amino Acid Sequence for Anti-EMAP II Antibody Variant Variable Region Affinity maturation was performed to induce a mutation from light chain and heavy chain variable regions of BAP015-hum03 antibody (commissioned to Bioatla LLC), for the purpose of obtaining an anti-EMAP II antibody variant having a higher antigen affinity, a higher effect of inhibiting TNF-α secretion and a higher effect of treating EMAP II-mediated diseases compared to a known human anti-EMAP II antibody (BAP015-hum03) (Korean Patent Publication No. 2012-0118918).

A sequence of the BAP015-hum03 antibody variant obtained above was analyzed to identify an amino acid sequence of a complementary determining region (CDR) of an antibody variable region for each of antibody variants (Table 1).

TABLE 1

| No. | Classification | Amino acid sequence | SEQ ID NO: |
|---|---|---|---|
| 1 | L-CDR1 | KASQDVSTAVA | SEQ ID NO: 7 |
| 2 | L-CDR2a | SASYRYT | SEQ ID NO: 8 |
| 3 | L-CDR2b | SASYRYW | SEQ ID NO: 9 |
| 4 | L-CDR2c | SASYGYT | SEQ ID NO: 10 |
| 5 | L-CDR3 | QQHYSIPYT | SEQ ID NO: 11 |
| 6 | H-CDR1 | GYTFTSYTMH | SEQ ID NO: 12 |
| 7 | H-CDR2a | YINPSSGFTNYNQKFKD | SEQ ID NO: 13 |
| 8 | H-CDR2b | YINPRSGFTNYRQKFKH | SEQ ID NO: 14 |
| 9 | H-CDR2c | YTNPSSGFTNYTQKFKD | SEQ ID NO: 15 |
| 10 | H-CDR3 | RFAY | SEQ ID NO: 16 |

The light chain CDR1, CDR2 and CDR3 regions of BAP015-hum03 antibody consist of L-CDR1, L-CDR2a and L-CDR3 amino acid sequences, respectively, and the heavy chain CDR1, CDR2 and CDR3 regions thereof consist of H-CDR1, H-CDR2a and H-CDR3 amino acid sequences, respectively. As a variable region of BAP015-hum03 antibody variant, a light chain variable region containing L-CDR1 (SEQ ID NO: 7), L-CDR2b (SEQ ID NO: 9) and L-CDR3 (SEQ ID NO: 11) was named BAP072-LC-T056W; and a light chain variable region containing L-CDR1 (SEQ ID NO: 7), L-CDR2c (SEQ ID NO: 10) and L-CDR3 (SEQ ID NO: 11) was named BAP072-LC-R54G, respectively, wherein a heavy chain variable region containing H-CDR1 (SEQ ID NO: 12), H-CDR2b (SEQ ID NO: 14) and H-CDR3 (SEQ ID NO: 16) was named BAP072-CPS-15-HC; and a heavy chain variable region containing H-CDR1 (SEQ ID NO: 12), H-CDR2c (SEQ ID NO: 15) and H-CDR3 (SEQ ID NO: 16) was named BAP072-CPS-08-HC, respectively.

With regard to light chain and heavy chain variable regions of the BAP015-hum03 antibody and the BAP015-hum03 antibody variant prepared above, the entire amino acid sequences thereof are as follows (Table 2).

TABLE 2

| | Peptide name | CDR constitution | Amino acid sequence | | Mutation |
|---|---|---|---|---|---|
| Light chain variable region | BAP015-hum03-LC (SEQ ID NO: 1) | L-CDR1 L-CDR2a L-CDR3 | AIQLTQSPSS ITCKASQDVS GKAPKLLIYS RFSGSGSGTD EDFAVYYCQQ G | LSASVGDRVT TAVAWYQQKP ASYRYTGVPS FTFTISRLEP HYSIPYTFGQ | Reference sequence |

TABLE 2-continued

|  | Peptide name | CDR constitution | Amino acid sequence | Mutation |
|---|---|---|---|---|
|  | BAP072-LC-T056W (SEQ ID NO: 3) | L-CDR1 L-CDR2b L-CDR3 | AIQLTQSPSS LSASVGDRVT ITCKASQDVS TAVAWYQQKP GKAPKLLIYS ASYRYWGVPS RFSGSGSGTD FTFTISRLEP EDFAVYYCQQ HYSIPYTFGQ G | T056W |
|  | BAP072-LC-R54G (SEQ ID NO: 5) | L-CDR1 L-CDR2c L-CDR3 | AIQLTQSPSS LSASVGDRVT ITCKASQDVS TAVAWYQQKP GKAPKLLIYS ASYGYTGVPS RFSGSGSGTD FTFTISRLEP EDFAVYYCQQ HYSIPYTFGQ G | R054G |
| Heavy chain variable region | BAP015-hum03-HC (SEQ ID NO: 2) | H-CDR1 H-CDR2a H-CDR3 | EVQLVQSGAE VKKPGATVKI SCKVSGYTFT SYTMHWVRQA PGQGLEWMGY INPSSGFTNY NQKFKDRVTI SADKSISTAY LQWSSLKASD TAMYYCASRF AYWGQG | Reference sequence |
|  | BAP072-CPS-15-HC (SEQ ID NO: 4) | H-CDR1 H-CDR2b H-CDR3 | EVQLVQSGAE VKKPGATVKI SCKVSGYTFT SYTMHWVRQA PGQGLEWMGY INPRSGFTNY RQKFKHRVTI SADKSISTAY LQWSSLKASD TAMYYCFSRF AYWGQG | S054R, N061R, D066H, A097F |
|  | BAP072-CPS-08-HC (SEQ ID NO: 6) | H-CDR1 H-CDR2c H-CDR3 | EVQLVQSGAE VKKPGATVKI SCKVSGYTFT SYTMHWVRQA PGQGLEWMGY TNPSSGFTNY TQKFKDRVHI SADKSISTAY LQWSSLKASD TAWYYCASRF AYWGQG | I051T, N061T, T069H, M093W |

As can be seen in the table above, it was identified for the BAP015-hum03 antibody variant obtained from affinity maturation that both a light chain and a heavy chain thereof hold the identical CDR1 and CDR3 to a parent antibody and both the light chain and the heavy chain thereof have one to three amino acid substitution mutations developed at a sequence of CDR2.

Example 1-2. Preparation for Expression Vector of Anti-EMAP II Antibody Variant Gene A light chain variable region (SEQ ID NO: 1) and a heavy chain variable region (SEQ ID NO: 2) of an anti-EMAP II parent antibody, as well as a light chain variable region (SEQ ID NO: 3 or SEQ ID NO: 5) and a heavy chain variable region (SEQ ID NO: 4 or SEQ ID NO: 6) of an antibody variant obtained in Example 1-1, were cloned into each of the mammal expression vector pBAK2b (BioAtla LLC) systems, respectively.

In the vector, each light chain variable region was fused with a frame for a human kappa constant region, and a heavy chain variable region was fused with a frame for a human IgG1 constant region. Also, in the vector, a leader peptide sequence for secretion of a full-length IgG1 antibody in a medium was added into a gene. A gene cloning method is the same as those known to those skilled in the art.

In result, each of antibodies BAP072-EMAP II-1, BAP072-EMAP II-2, BAP072-EMAP II-3 and BAP072-EMAP II-4 was produced in such a way that a light chain variable region and a heavy chain variable region were combined respectively (Table 3).

TABLE 3

| Antibody name | Light chain variable region | Heavy chain variable region | Constant region |
|---|---|---|---|
| BAP015-hum03 | BAP015-hum03-LC | BAP015-hum03-HC | Human kappa light chain constant region and Human IgG1 heavy chain constant region |
| BAP072-EMAP II-1 | BAP072-LC-T056W | BAP072-CPS-15-HC | |
| BAP072-EMAP II-2 | BAP072-LC-T056W | BAP072-CPS-08-HC | |
| BAP072-EMAP II-3 | BAP072-LC-R54G | BAP072-CPS-15-HC | |
| BAP072-EMAP II-4 | BAP072-LC-R54G | BAP072-CPS-08-HC | |

Five clones of each vector were subjected to sequencing to identify an incorporation and sequence of LC and HC reading frames within an expression vector, after which three clones were selected for an expression test within CHO cells. After that, a glycerol stock of the three clones was prepared, after which a plasmid DNA without endotoxin was prepared for the expression test within the CHO cells.

Example 1-3. Detection of Anti-EMAP II Antibody Variant after Transformation into CHO Cells With regard to CHO—S cells, transformation was performed by using the plasmid DNA obtained above.

First of all, the CHO—S cells (CD-CHO) (Invitrogen) were transferred into a single-layer culture product within serum-supplement D-MEM (Dulbecco's Modified Eagle Medium) (Invitrogen) one week before transfection. 0.4× $10^5$ cells were plated into 100 μl of the serum-supplement D-MEM per transfection sample in a 96-well format one day before transfection. A DNA-lipofectamine complex was prepared for each transfection sample. 0.2 μg of plasmid DNA was diluted in 25 μl of Opti-MEM reduced serum medium and mixed therein. 0.5 μl of lipofectamine 2000 (Invitrogen) was diluted in 25 μl of Opti-MEM reduced serum medium. The resulting one was mixed and incubated for 5 minutes at room temperature. The diluted DNA and lipofectamine were mixed together and incubated for 20 minutes at room temperature. 50 μl of the DNA-lipofectamine complex was added into each well containing the cells and the medium and softly mixed together. The resulting cells were incubated overnight under the condition of 5% $CO_2$ and 37° C. The medium was removed from each well by suction, after which 100 μl of serum-supplement D-MEM was added into each well.

In 48 hours after transfection, a cell culture supernatant was collected therefrom, after which ELISA was performed to quantify a concentration of recombinant IgG in such collected cell culture supernatant. First of all, IgG of recombinant BAP015-hum03, BAP072-EMAP II-1, BAP072-EMAP 11-2, BAP072-EMAP 11-3 and BAP072-EMAP II-4 was captured in the cell culture supernatant by using an anti-human Fc antibody fixed to the plate. A bound recombinant IgG was detected with an anti-human IgG HRP conjugate, and quantified by using a commercial human IgG as a reference standard.

More particularly, a Nunc-Immuno Maxisorp 96-well plate (Nalge Nunc) containing 100 μl of affinity-purified Fc specific goat anti-human IgG (Sigma) at to μg/μl was coated in a coating solution, after which the plate was sealed up and incubated overnight at 4° C. After that, the plate was washed with 200 μl of washing solution by stirring at 200 rpm for 5 minutes at room temperature. Then, 200 up of blocking solution was added thereinto and stirred at 200 rpm for 1 hour at room temperature. A purified human serum IgG (Invitrogen) at a standard concentration of 100 μg/μl or 100 μl of the supernatant obtained from transfection was redundantly added thereinto. The resulting one was stirred at 200 rpm for 1 hour at room temperature, and washed twice with 200 μl of washing solution at 200 rpm for 5 minutes at room temperature. 100 μl of 1:5000 dilution of HRP-conjugated affinity-purified goat anti-human antibodies (Promega) in blocking solution was added into each well, then stirred at 200 rpm for one hour at room temperature, and then washed three times with 200 μl of washing solution at 200 rpm for five minutes at room temperature. Sigma TMB substrate was added into each well and incubated at room temperature. After that, 100 μl of 1N HCl was added thereinto to finish a reaction and read at 450 nm.

Example 1-4. Isolation and Purification of Anti-EMAP II Antibody Variant

The CHO—S cell lines with each DNA transformed therein were cultured as described above, after which culture fluid was collected therefrom and protein A agarose bead (Invitrogen) was loaded thereon, such that each antibody was allowed to bind thereto. Then, the bead was washed with PBS, then eluted with 0.1M glycine (pH 3.0), then neutralized with 1M Tris-HCl (pH 8.0), and then dialyzed again with PBS containing 20% glycerol, such that antibodies (BAP015-hum03, BAP072-EMAP II-1, BAP072-EMAP 11-2, BAP072-EMAP 11-3 and BAP072-EMAP II-4) were identified with SDS-PAGE gel under the non-reducing conditions and under the reducing conditions, respectively (FIG. 1). The antibodies obtained were kept at 70° C.

Example 2. Identification of Antigen-Binding Ability of Anti-EMAP II Antibody Variant Example 2-1. Comparison of Antigen-Binding Abilities of Antibody Variants by ELISA A matrix experiment was set up as follows, in order to identify a linear scope for comparing the antigen-binding abilities of BAP015-hum03, BAP072-EMAP II-1, BAP072-EMAP 11-2, BAP072-EMAP 11-3 and BAP072-EMAP II-4 antibodies.

Each well of a 96-well plate was coated with 100 μl of EMAP II antigens at a concentration of 1 μg/ml, and incubated at 37° C. for 2 hours. The coated antigens were blocked with 5% BSA and washed with washing buffer solution. Then, the antigens were treated with a dilution of BAP015-hum03, BAP072-EMAP II-1, BAP072-EMAP II-2, BAP072-EMAP II-3 and BAP072-EMAP II-4 antibodies (at 0.625, 1.25, 2.5, 5, 10, 20, 50, 100, 500 and 1000 μg/ml), and incubated for 2 hours. The resulting ones were washed 3 times with washing buffer solution, then treated with anti-IgG-HRP antibodies, and then incubated for 1 hour. Then, the resulting ones were washed 3 times with washing buffer solution, and treated with a substrate for 30 minutes at room temperature. Color development was performed, after which stop solution was inserted thereinto, such that absorbance was measured at a wavelength of 450 nm to test an antigen-binding ability of the antibodies.

Figure 2:
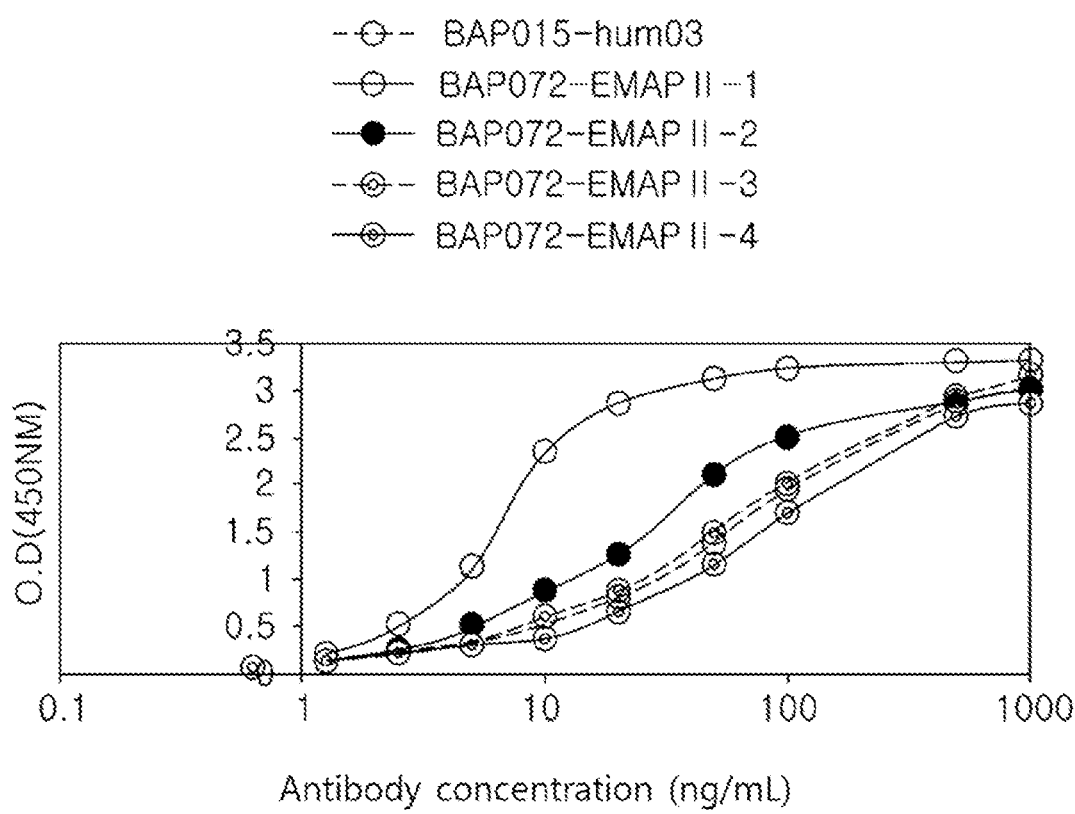
FIG. 2 shows results of comparing the antigen-binding abilities of the inventive anti-EMAP II antibody by using ELISA.

In result, in case of BAP072-EMAP 11-2, BAP072-EMAP II-3 and BAP072-EMAP II-4 antibodies, a concentration of antibodies to reach O.D 2.5 is about 100 ng/ml or more, thus showing a level of binding ability equal to BAP015-hum03 antibody. However, in case of BAP072-EMAP II-1 antibody, the concentration of antibodies to reach O.D 2.5 is no more than about to ng/ml, thus showing that an antigen-binding ability thereof is about to times more than other antibodies (FIG. 2).

Example 2-2. Comparison of Antigen-Binding Abilities of Anti-EMAP II Antibody Variants Through SPR Analysis A surface plasmon resonance (SPR) method was used to further compare the antigen-binding abilities between BAP015-hum03 and BAP072-EMAP II-1. Reichert SR7500DC system (Reichert Technologies, Depew, N.Y.) was used for SPR, and Scrubber2 software was used for data collection. 2.5 μg of EMAP II protein was fixed to PEG chip (Reichert Technologies), after which BAP015-hum03 and BAP072-EMAP II-1 antibodies were flowed thereinto to compare the binding abilities therebetween.

Figure 3:
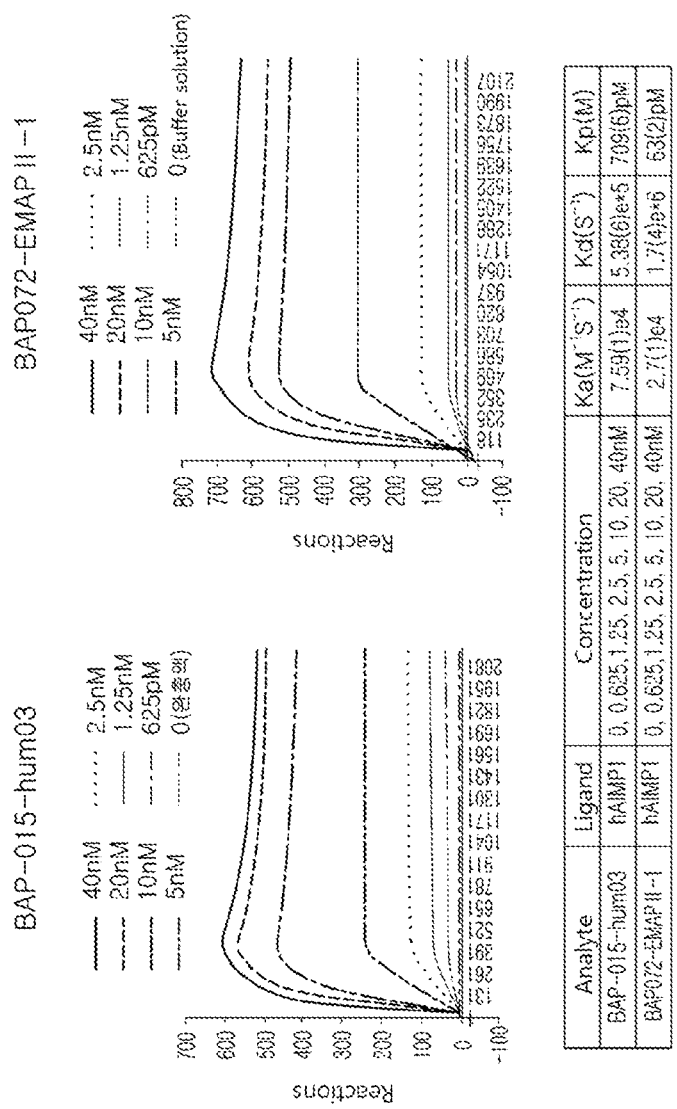
FIG. 3 shows results of comparing the antigen-binding abilities of the inventive anti-EMAP II antibody by using SPR assay.

In result, a $K_D$ value of BAP015-hum03 antibody is $7.09\times10^{-10}$ M and the $K_D$ value of BAP072-EMAP II-1 antibody is $6.3\times10^{-11}$ M, thus identifying that BAP072-EMAP II-1 shows an antigen-binding ability about to times more than a control group, i.e., BAP015-hum03, just as shown in the ELISA results above (FIG. 3).

Example 3. Therapeutic Effect on Mouse Arthritis

A collagen-induced arthritis (CIA) mouse model was used to identify an effect of the inventive anti-EMAP II antibody on treating arthritis. To prepare a model mouse, six-week-old pathogen free DBA/1 mice (female) were purchased from Orient Bio and kept until they became seven weeks old.

For primary immunization, 200 mg of native bovine type II collagen (Chondrex) was dissolved in too ml of to mM acetic acid and fully mixed by stirring at 1000 rpm for 12 hours at 4° C. with the same amount of complete Freund's adjuvant containing 200 mg of inactivated *Mycobacterium tuberculosis* (Sigma-Aldrich). 100 ml of a resulting mixture was intradermally injected into a basal region in each tail of seven-week-old female DBA/1 mice to perform primary immunization.

On 21st day after the primary immunization, the mice were boosted with 100 mg of bovine type II collagen in incomplete Freund's adjuvant (Sigma-Aldrich) to perform secondary immunization.

For 70 days after the primary immunization, the mice were observed once a week to evaluate the severity of their arthritis. A thickness of each mouse foot was measured with a vernier caliper. Two independent observers evaluated a total of four legs of each mouse and gave arthritis scores ranging from 0 to 5 (Table 4).

TABLE 4

| Arthritis scores | Symptoms |
|---|---|
| 0 | No sign of arthritis |
| 1 | One redness in feet or toes |
| 2 | Slight swelling in an ankle with a few individual toes swollen |
| 3 | Moderate swelling in an ankle |
| 4 | Severe enlargement of an entire ankle including toes |
| 5 | Inflammable limbs involving multiple joints |

In 14 days after secondary immunization, it was observed that CIA mice were completely developed. 50 mice, which had an arthritis score of more than 4 points, were equally divided into six groups (Group 1: normal control; Group 2: treated with vehicle; Group 3: treated with 5 mg/kg of BAP015-hum03; Group 4: treated with 1 mg/kg of BAP072-EMAP II-1; Group 5: treated with 2 mg/kg of BAP072-EMAP II-1; and Group 6: treated with 5 mg/kg of BAP072-EMAP II-1). Then, arthritis scores were measured for all the mice but the normal control group, after administering an intraperitoneal injection with the antibodies at a concentration marked in the groups a total of 4 times at an interval of once a week Arthritis scores were measured in a double-blind manner.

Figure 4:
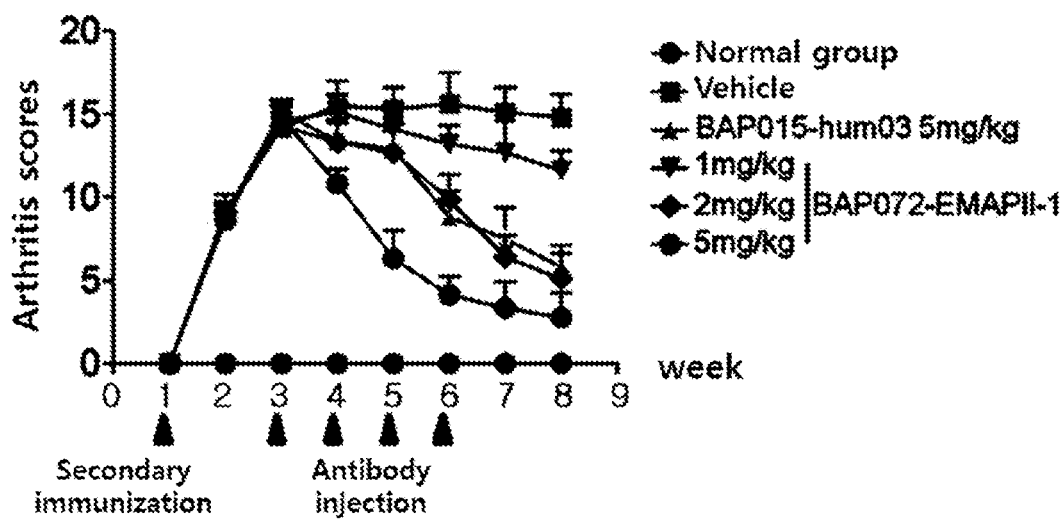
FIG. 4 shows an effect of the inventive anti-EMAP II antibody on inhibiting arthritis in a CIA mouse model.
Figure 4:
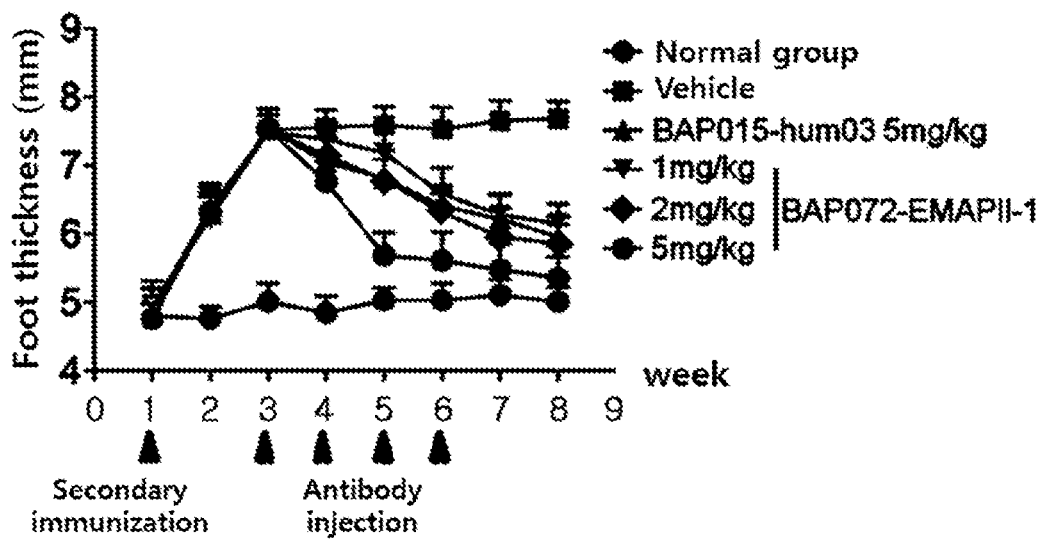

In result, it was identified that an arthritis symptom starts to be alleviated from one week after treatment with antibodies. When making a comparison between the groups treated with 5 mg/kg of the antibodies, BAP072-EMAP II-1 antibody started to show an excellent alleviation of arthritis and a great decrease in the thickness of swollen feet compared to the control group, i.e., BAP015-hum03 antibody from one week after treatment, thus achieving a therapeutic effect early on (FIG. 4). Furthermore, the therapeutic effect of the control group, i.e., 5 mg/kg of BAP015-hum03 antibody was similar to that of 2 mg/kg of BAP072-EMAP II-1 antibody according to the present invention, thus identifying that the present invention has an excellent therapeutic efficacy of achieving a level of alleviating arthritis similar to existing antibodies even in a low dose. As identified in Example 2, such results were based on an excellent antigen-binding capacity of BAP072-EMAP II-1 according to the present invention, thus proving that the present invention has an excellent efficacy of treating arthritis.

Example 4. Inhibitory Effect on Mouse TNF-α Secretion

A TNF-α level in serum of CIA mice treated with antibodies was investigated with ELISA, in order to identify an improved effect of the inventive anti-EMAP II antibody on inhibiting TNF-α secretion. ELISA was performed according to a manufacturer's instructions, after purchasing a mouse TNF-α ELISA kit (R&D systems, USA). Experiment methods such as preparation for the CIA mouse and a schedule for administering antibodies are the same as described in Example 3. Blood was sampled once a week from the CIA mice prepared in Example 3-1 to isolate serum therefrom, after which ELISA was performed for TNF-α.

Figure 5:
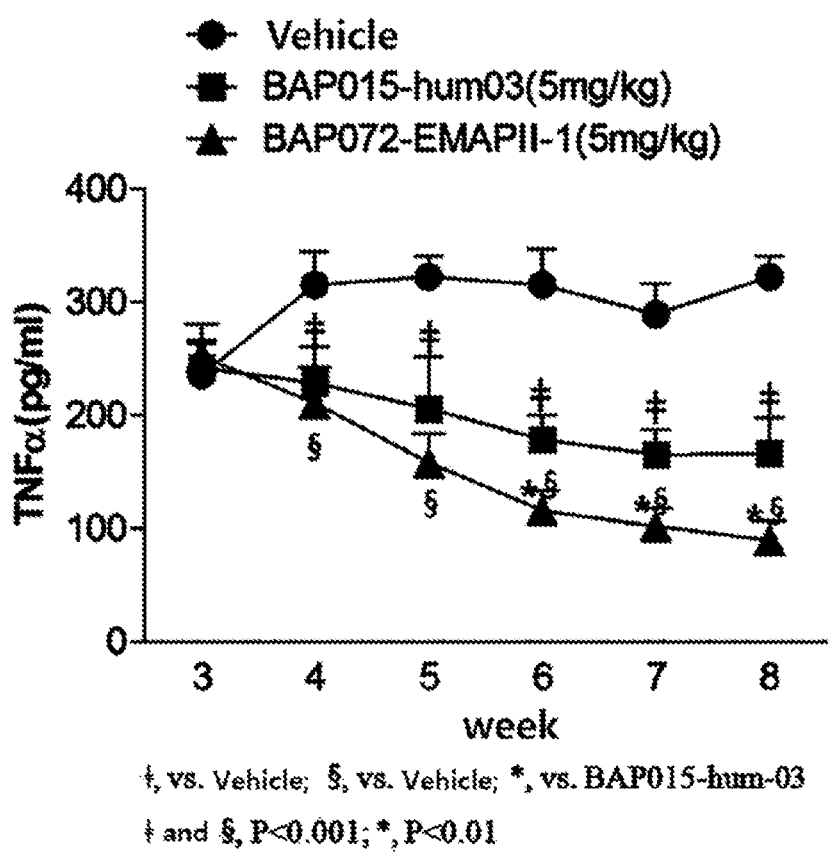
FIG. 5 shows an efficacy of the inventive anti-EMAP II antibody on inhibiting TNF-α secretion in the CIA mouse model.

In result, it was shown that both BAP015-hum03 and BAP072-EMAP II-1 antibodies tend to show a significant decrease in a TNF-α level, i.e., an inflammatory factor (FIG. 5). Out of them, when comparing the results of TNF-α level between BAP015-hum03 and BAP072-EMAP II-1, it was shown that BAP072-EMAP II-1 antibody of the present invention decreases the TNF-α level more remarkably than BAP015-hum03 antibody.

In other words, the BAP072-EMAP II-1 antibody of the present invention effectively inhibits TNF-α, i.e., a representative inflammation marker, thus showing an excellent effect of treating TNF-α-mediated diseases including arthritis.

The embodiments above show that the anti-EMAP II antibody variant or the antigen-binding fragment thereof according to the present invention has a much more antigen-binding capacity as well as a much more excellent effect on EMAP II-mediated diseases compared to EMAP II antibodies disclosed in the prior document. In particular, the anti-EMAP II antibody variant of the present invention has an excellent effect of inhibiting TNF-α and thus exhibits a remarkable effect of treating TNF-α-mediated diseases.

While specific portions of the present invention have been described in detail above, it is apparent to those having ordinary skill in the art that such detailed descriptions are set forth to illustrate exemplary embodiments only, but are not construed to limit the scope of the present invention. Thus, it should be understood that the substantial scope of the present invention is defined by the accompanying claims and equivalents thereto.

The invention claimed is:

1. An anti-EMAP II (endothelial monocyte activating polypeptide II) antibody or an antigen-binding fragment thereof, comprising a light chain variable region, containing a light chain CDR1 consisting of SEQ ID NO: 7, a light chain CDR2 consisting of SEQ ID NO: 9, and a light chain CDR3 consisting of SEQ ID NO: 11; and a heavy chain variable region, containing a heavy chain CDR1 consisting of SEQ ID NO: 12, a heavy chain CDR2 consisting of SEQ ID NO: 14, and a heavy chain CDR3 consisting of SEQ ID NO: 16.

2. The anti-EMAP II antibody or the antigen-binding fragment thereof according to claim 1, wherein the antibody comprises a light chain variable region consisting of SEQ ID NO: 3; and a heavy chain variable region consisting of SEQ ID NO: 4.

3. The anti-EMAP II antibody or the antigen-binding fragment thereof according to claim 1, characterized in that the antibody is a humanized antibody.

4. The anti-EMAP II antibody or the antigen-binding fragment thereof according to claim 1, wherein the antibody comprises a kappa or human IgG-derived constant region.

5. The anti-EMAP II antibody or the antigen-binding fragment thereof according to claim 1, characterized in that the antigen binding fragment is Fab, F(ab'), F(ab')2 or Fv.

6. A nucleic acid molecule for coding the antibody or the antigen-binding fragment thereof according to claim 1.

7. A recombinant vector comprising the nucleic acid molecule according to claim 6.

8. A transformed cell comprising the recombinant vector according to claim 7.

9. A method for preparing an anti-EMAP II antibody or an antigen-binding fragment thereof, comprising a step of expressing the anti-EMAP II antibody or the antigen-binding fragment thereof by culturing the transformed cell according to claim 8 and (ii) a step of isolating the anti-EMAP II antibody or the antigen-binding fragment thereof.

10. A pharmaceutical composition, comprising the anti-EMAP II antibody or the antigen-binding fragment thereof according to claim 1 as an active ingredient.

11. A composition for detecting an EMAP II antigen, comprising the anti-EMAP II antibody or the antigen-binding fragment thereof according to claim 1 as an active ingredient.

12. A kit for detecting an EMAP II antigen, comprising the anti-EMAP II antibody or the antigen-binding fragment thereof according to claim 1 as an active ingredient.

13. A method for detecting an EMAP II antigen in a sample, comprising a step of bringing the anti-EMAP II antibody or the antigen-binding fragment thereof according to claim 1 into contact with the sample.

14. A method for treating EMAP II-mediated disease, including administering a therapeutically effective amount of a composition comprising the anti-EMAP II antibody or the antigen binding fragment thereof according to claim 1, wherein the EMAP II-mediated disease is rheumatoid arthritis.

* * * * *